(12) United States Patent
Li

(10) Patent No.: US 7,241,626 B2
(45) Date of Patent: Jul. 10, 2007

(54) ISOLATION AND CONFIRMATION OF ANALYTES FROM TEST DEVICES

(75) Inventor: Jingkun Li, Bear, DE (US)

(73) Assignee: Strategic Diagnostics Inc., Newark, DE (US)

( * ) Notice: Subject to any disclaimer, the term of this patent is extended or adjusted under 35 U.S.C. 154(b) by 0 days.

(21) Appl. No.: 10/712,419

(22) Filed: Nov. 12, 2003

(65) Prior Publication Data

US 2004/0132211 A1    Jul. 8, 2004

Related U.S. Application Data

(60) Provisional application No. 60/425,839, filed on Nov. 12, 2002.

(51) Int. Cl.
*G01N 33/53* (2006.01)
(52) U.S. Cl. ............... 436/514; 436/518; 436/524; 436/530; 436/541; 436/807; 435/7.1; 435/7.93; 435/7.94; 435/287.7; 435/287.9
(58) Field of Classification Search .............. 435/7.1, 435/7.93, 7.94, 287.7, 287.9, 970; 436/518, 436/524, 530, 541, 807
See application file for complete search history.

(56) References Cited

U.S. PATENT DOCUMENTS

| 3,811,840 | A |   | 5/1974  | Bauer et al. |
| 3,811,841 | A |   | 5/1974  | Kassel |
| 4,094,647 | A |   | 6/1978  | Deutsch et al. |
| 4,235,601 | A |   | 11/1980 | Deutsch et al. |
| 4,361,537 | A |   | 11/1982 | Deutsch et al. |
| 4,366,241 | A |   | 12/1982 | Tom et al. |
| 4,415,700 | A |   | 11/1983 | Batz et al. |
| 4,435,504 | A |   | 3/1984  | Zuk et al. |
| 4,695,393 | A | * | 9/1987  | Chagnon et al. .......... 252/62.54 |
| 4,822,566 | A |   | 4/1989  | Newman |
| 5,491,068 | A | * | 2/1996  | Benjamin et al. .......... 435/7.32 |
| 5,874,216 | A |   | 2/1999  | Mapes |
| 5,900,379 | A | * | 5/1999  | Noda et al. .................. 436/518 |
| 5,994,145 | A |   | 11/1999 | Stave |
| 6,001,658 | A |   | 12/1999 | Fredrickson |
| 6,096,563 | A |   | 8/2000  | Hajizadeh et al. |
| 6,140,136 | A |   | 10/2000 | Lee |
| 6,277,818 | B1 | * | 8/2001 | Mazar et al. ................... 514/9 |
| 6,365,417 | B1 |   | 4/2002 | Fleming et al. |
| 6,376,195 | B1 |   | 4/2002 | Mapes |
| 6,423,550 | B1 |   | 7/2002 | Jenkins et al. |
| 6,607,922 | B2 | * | 8/2003 | LaBorde ..................... 436/514 |

\* cited by examiner

*Primary Examiner*—Bao-Thuy L. Nguyen
(74) *Attorney, Agent, or Firm*—Kilpatrick Stockton LLP

(57) ABSTRACT

Methods, articles, and kits for obtaining elevated concentrations of a substance from a sample that has become bound, for example by providing a positive test result in an immunoassay or other binding assay. The concentrated substance is optionally subjected to further processing or analysis, for example to confirm the identity of the substance, such as a pathogenic organism in a food sample.

23 Claims, No Drawings

ISOLATION AND CONFIRMATION OF ANALYTES FROM TEST DEVICES

CROSS-REFERENCE TO RELATED APPLICATIONS

This application claims priority to U.S. Provisional Application No. 60/425,839 filed Nov. 12, 2002 which is incorporated herein by reference.

FIELD OF THE INVENTION

The present invention relates to the field of microbiology and more specifically relates to methods, articles, and kits for concentrating an analyte. In particular, the invention relates to the concentration of an analyte using an assay such as an immunoassay to facilitate confirmation of a positive assay result.

BACKGROUND OF THE INVENTION

Various approaches have been described for performing assays to determine the presence or concentration of a specific analyte, such as a food or soil contaminant. Many assays determine the presence or concentration of analyte in a sample by relying on the binding of an analyte by another molecule or group of molecules. Examples of such molecules include but are not limited to analyte receptors, antibodies to the analyte, and other molecules and combinations of molecules with binding affinity for the analyte. One type of assays is the immunoassay, which is based on the highly specific binding between an antibody and an antigen recognized by the antibody.

When a binding assay is utilized to determine the presence or concentration of an analyte in a sample, it is often desirable to conduct further analysis to confirm the accuracy of the "positive" indication and rule out problems such as crossreactivity, which could lead to an inaccurate positive result. For example, immunoassays are often used in lateral flow devices such as test strips to determine the presence in foods of contaminants such as pathogens. However, additional confirmation of a positive test result is sometimes desired and in some cases required by governmental regulation to prevent the unnecessary recall and destruction of large quantities of the substance being tested, such as food products.

In some cases, the first step for confirmation of a positive result is to obtain a large quantity of the substance that is causing the positive result, possibly in pure state and free from similar microorganisms. For example, in some cases in which the contaminant of a food sample is a biological pathogen or microorganism (for example, a protozoan, bacteria, or virus) the contaminant can be cultured using conventional microbiological techniques to produce large quantities of the pathogen for subsequent analysis. However, suspected pathogens are often present among other non-pathogenic microbes in the sample, thus complicating the analysis. Obtaining a pure isolate or a sufficiently high concentration of an analyte such as a pathogenic contaminant can be tedious, expensive and time consuming.

Microorganisms in contaminated food that cause gastrointestinal infections are extremely common worldwide. Food contamination, often referred to as food poisoning, can have symptoms such as nausea, vomiting, abdominal pain, diarrhea and fever. If left untreated, some contaminants can cause death, especially in children, the elderly, or in immunocompromised individuals. Food contaminants such as some varieties of *Staphylococcus aureus* and *Bacillus cereus* can produce enterotoxins, which can cause symptoms such as nausea and vomiting. Some viruses such as rotaviruses and Norwalk virus, and some protozoans such as *Giardia lamblia* can cause diarrhea by irritating or destroying the intestinal mucosa. Dysentery, an infection of the colon that can cause abdominal pain, hemorrhagic diarrhea, fever and dehydration can be caused by organisms such as *Salmonella, Shigella, Campylobacter, Escherechia coli*, and *Clostridium*. *E. coli* O157 is a particularly pathogenic strain of *E. coli* that has been found to be a contaminant of meat and other food and beverage products.

One method for confirming a positive test result for the presence of *Escherechia coli* O157 in a sample of food or beverage involves culturing microorganisms in the sample to produce large quantities. The microorganisms are then separated from each other and from other components of the culture. One technique for performing this procedure is the use of magnetic beads coated with an antibody specific for *E. coli* O157. The culture is poured over a column containing the beads and absorbed to the surface of the beads. Beads are then collected using a magnet, washed, and eluted to obtain a solution in which any *E. coli* present will have a concentration higher than the original sample. The high concentration solution can then be streaked on selective agar plates for growth and inspection to determine the presence of *E. coli* O157 colonies. This procedure is not only expensive, but is also time-consuming, an important consideration when confronted with a decision to suspend or to recall distribution of a widely distributed food product.

Thus, what is needed in the art is a rapid method for confirming the results of an assay. What is further needed in the art is a rapid method for obtaining a sample in which the concentration of the microbes, molecules, or other objects that caused a "positive" indication of an assay is increased as compared to an original sample.

SUMMARY OF THE INVENTION

The invention solves the problems of the prior art by providing methods for concentrating or obtaining elevated concentrations of a substance from a sample. In some embodiments, the sample has provided a positive test result in an immunoassay or other binding assay. The concentrated substance is then optionally subjected to further analysis to characterize the substance, for example, confirming the identity of a pathogenic organism in a food sample. The concentrated substance is obtained by applying the sample to a surface that binds the substance such as, for example, an immunoassay test strip upon which the analyte migrates to a predetermined location and is bound. The analyte is thereby concentrated on the surface or, optionally, one or more specific portions of the surface. In some embodiments, all or a portion of the bound analyte is then removed from the test strip and characterized. Optionally, the bound analyte may be subjected to procedures that increase its concentration, such as culturing a microorganism for subsequent identification and analysis.

In some embodiments, the method relies upon the immobilization of the substance as part of a binding assay, such as an immunoassay, in which the existence of a "positive" indication results from the binding or immobilization of a substance with one or more surfaces having a binding affinity for the substance. Due to this binding affinity, the surface has the substance bound or otherwise affixed thereto. The substance bound or affixed to the surface is optionally used to prepare a solution or composition with an elevated concentration of the substance. In some embodiments, these methods include separating the surface to which the substance is bound from other portions of an article or device to which the surface is attached. In some embodiments, these methods include the further step of transferring the bound or immobilized substance to conditions effective to cause proliferation, replication, reproduction, or any other process that causes the amount or the concentration of the substance to increase.

The procedures outlined above have numerous uses, and the invention includes methods for performing those uses. For example, the invention includes methods of isolating or purifying substances using similar procedures. In some embodiments, the invention includes methods for isolating or purifying substances that have shown crossreactivity with a specific assay, antibody, or other binding compound (for example, substances that can produce a false positive result in an immunoassay). The invention also includes methods for determining the purity of a culture. The invention also includes methods for purifying a culture.

The invention further includes methods of identifying a substance, characterizing a substance, or both, including but not limited to determining the chemical or biological identity of a substance. In some embodiments of such methods, the substance is first isolated or concentrated upon a surface such as that used in a binding assay, then subjected to further processing that allows determination of the identity of the substance. In some embodiments, the substance is an organism such as a bacteria, fungus, protozoan, algae, or plankton and the further processing involves transferring the bound or immobilized substance to conditions that allow proliferation or reproduction of the organism to such degree that the identity of the organism can be determined by microscopic inspection, analytical testing, or other concentrations thereof. In some embodiments, substances (for example, bacteria) isolated or concentrated upon the surface are transferred (e.g., plated) directly from the surface to environments that will allow proliferation of the substance (for example, agar plates that will allow growth of colonies of a bacteria). In some embodiments, the substance or the surface containing the substance is placed in media to promote proliferation of the substance, then transferred. In some embodiments, a culture is plated, and individual colonies resulting from the plating are isolated and further plated. In some embodiments, these methods allow confirmation of a positive indication in a binding assay.

The invention further includes binding assay methods that include the further steps of concentrating the bound substance. In some embodiments, the concentrated bound substance is then subjected to further analysis to characterize or to identify the substance including, for example, analyses that can provide confirmation of the results of the assay. The invention further includes articles and kits that can be used to perform any of the above methods.

DETAILED DESCRIPTION OF THE PREFERRED EMBODIMENTS

Methods, articles, and kits are provided for obtaining elevated concentrations of a substance from a sample that has exhibited a positive test result in a binding assay upon a surface. In some embodiments, the concentrated substance is then subjected to further analysis to confirm the identity of the substance. The concentration of the substance is obtained by applying the sample to a binding assay and allowing the substance to bind. The substance is present at the site of binding in a concentrated form. All or a portion of the concentrated substance is then removed from the surface. For example, in some embodiments in which the surface is an immunoassay lateral flow device (LFD) or test strip, the portion of the test strip to which the substance is bound is removed, or the analyte is detached from the test strip. The substance is then optionally cultured and/or subjected to subsequent identification and analysis. In some embodiments, use of a test strip in which the sample migrates across a binding surface allows separation of the concentrated substance from non-pathogenic forms of similar analytes during migration along the test strip and is therefore present at the binding location in a purer form than in the sample. In some embodiments the substance is then removed from a test strip by contacting the site of binding on the test strip with a means for the transfer of microorganisms, such as by swabbing the site or streaking the location upon agar.

Definitions

Throughout this application, the term "substance" shall be used in its broadest definition and shall include any molecules, objects, or cells of any type or size, or any possible combinations thereof. Substances can be in any form including, but not limited to solid, semisolid, liquids, wet or dry mixture, gas, solution, suspension, or combinations thereof. Substances include molecules of any type and size and any combinations of molecules. Cells include all cell types and taxa, including but not limited to all prokaryotic and eukaryotic cells and irrespective of whether the cells are in natural state or altered by genetic engineering, transformation, or any other processes. Cells also include but are not limited to cells from natural sources and cells cultured in vitro. Cells can be living or dead. Any combinations of different types of cells can be used. Objects can be of any size, shape, and composition. Examples of objects include, but are not limited to, cell fragments, cell debris, fragments of cell walls, fragments of viral walls, organelles and other cell components, tablets, viruses, prions, vesicles, liposomes, capsules, and nanoparticulates. The term "substance" also includes any combination of the foregoing substances.

Throughout this application, the terms "concentrate," "concentration," and "concentrating" shall be used to describe methods of obtaining higher concentrations of higher amounts of a substance than that found in an original sample. The method relies upon the immobilization of the substance through binding, such as the binding that occurs as part of a binding assay. For example, in some embodiments involving binding assays, the existence of a "positive" indication is due to the binding or immobilization of a substance to one or more surfaces having a binding affinity for the substance. Due to this binding affinity, the surface has the substance bound or otherwise affixed thereto. The substance bound or affixed to the surface is used in some embodiments to prepare a solution or composition with an elevated concentration of the substance. The invention thus includes methods of concentrating any substance. In some embodiments, these methods include the further step of transferring the bound or immobilized substance to conditions effective to cause proliferation, replication, reproduction, or any other process that causes the amount or the concentration of the substance to increase.

Throughout this application, the term "analyte" includes any substance for which the presence or concentration is detected in any assay method or device. The analyte may be any substance. Some examples of analytes include but are not limited to prokaryotic or eukaryotic cells of any type, bacteria, protozoans, and other organisms of any type, viruses, prions, haptens, hormones, peptides, proteins, nucleic acids such as deoxyribonucleic acid (DNA) and ribonucleic acids (RNA), toxic chemicals, pesticides, petroleum components, metabolites of the aforementioned materials and other substances of either natural or synthetic origin that are of diagnostic interest. Analytes also include classes or groups of substances for which the presence or concentration of one or more members of the class or group is indicated by an assay.

Throughout this application, the term "suspected analyte" means any substance that has provided a positive indication in an assay for a specific analyte. A suspected analyte may or may not be an analyte.

Unless specifically indicated otherwise, the terms "bind," "binding," "bound," and "bond" throughout this application, all refer to any type of immobilization, formation of a complex, fixation, or attachment between two or more substances, between a substance and one or more surfaces, or a combination thereof, regardless of the mechanism or mechanisms of attachment involved. Examples of mechanisms include, but are not limited to, formation of antibody-antigen complexes, covalent bonding, ionic bonding, hydrogen bonding, van der Walls attraction, absorption, and adsorption.

Throughout this application, the term "binding partner" includes any substance capable of forming a bond with another substance. Some substances have multiple binding partners. Some substances are binding partners to multiple other substances. Where reference is made to a "binding partner" for a specified substance or group of substances, that reference refers to a substance that is capable of forming a bond with the specified substance or group of substances. Examples of binding partners include, but are not limited to, antibodies having an affinity to a given substance, enzymes capable of binding a substrate substance, receptors having an affinity for a ligand substance, antigens that are binding partners for antibody substances, and nucleic acids capable of hybridizing other nucleic acids.

Throughout this application, the term "binding assay" is an assay for at least one analyte which may be detected by the binding between the analyte and a binding partner. Binding assays are generally useful for the in vitro determination of the presence and/or concentration of analyte in a solution or composition. Any type of binding assays useful with any type of solution or composition may be used. Examples of compositions for which binding assays are used include, but are not limited to, biological samples, body fluids from any organisms, food products, pharmaceutical or cosmetic products, forensic samples, and environmental samples. In some embodiments, the assay determines the presence or concentration of pathogens in food or materials to be used as food. In some embodiments, the assay determines the presence or concentration of specific hormones, peptides, proteins, therapeutic drugs, illegal substances, or toxic drugs in blood, urine, or other bodily fluids or tissues of humans or other organisms. Binding assays include but are not limited to assays that use any type of detection systems such as enzyme-catalyzed chromogenic reactions, radionuclides, chemiluminescence, bioluminescence, fluorescence, fluorescence polarization, as well as a variety of potentiometric and optical biosensor techniques and visual labels such as latex beads, gold particles and carbon black.

Binding Assays

The invention may be used with any type of binding assay or any other analytical method that involves binding or immobilization of an analyte or other substance. Examples of such assays include, but are not limited to, immunoassays, DNA hybridization assays, and assays that involve binding partners for analyses. In some embodiments, the binding assay involves a binding partner for the analyte, in which the binding partner is immobilized or bound to a solid surface such as a plate, a glass slide a lateral flow device (e.g. a test pad or test strip), a bead, a plastic tube, a well, a membrane on a test strip, a pad, or a surface of an object. Examples of such objects are described, for example, in U.S. Pat. Nos. 3,811,841; 3,811,840; 4,094,647; 4,235,601; 4,366,241; 4,435,504; 4,361,537; 4,415,700; 4,822,566; 5,994,145; 5,874,216; 6,096,563; and 6,376,195. In some embodiments, the binding partner is bound to a specific location or zone on or along the surface of an object. Isolation or concentration in a specific zone is commonly used with test strips. As a result, when an analyte or suspected analyte binds with a binding partner, the analyte or suspected analyte is also immobilized in a surface or zone of the object.

Binding assays, especially immunoassays, are often described as either competitive or non-competitive. However, any binding assay may be used, regardless of whether it can be categorized as competitive, noncompetitive, both, or neither. Some non-competitive assays utilize antibodies or other binding partners in substantial excess over the possible concentration of analyte to be determined in the assay. Some competitive assays involve placing a sample suspected of containing an analyte together with an analyte analog conjugated to an enzyme or other signal producing substance, and the competition of these species for a limited number of binding sites provided by the antibody. Due to competition between unbound analyte and analyte analog-enzyme conjugate for binding sites on the binding partner, as the analyte concentration increases, the amount of unbound analyte analog-enzyme conjugate increases, thereby decreasing the observed signal in the location in which the binding partner is located. The product of the enzyme reaction may then be measured using an instrument such as a spectrophotometer. In some embodiments of competitive assays, an enzyme-labeled antigen or antibody acts in competition with an analyte for a reaction site on a bead, pad or surface. The reaction sites in these embodiments have a molecule that is a binding partner for both the analyte and the enzyme-labeled antigen or antibody. Analyte present in the sample competes with the enzyme-labeled molecule for binding to the binding partner, and the presence or concentration of the analyte is determined based on the presence and degree of enzyme activity at the site. In this embodiment, a higher concentration of analyte weakens the degree of enzyme activity at the site. The "sandwich" assay is one example of a non-competitive assay. In one embodiment of the sandwich assay, the antibody or antigen to be determined is "sandwiched" between at least two molecules by a reaction with a solid surface coated with or otherwise bound to a binding partner for the analyte (for example, an immunological species with affinity for the analyte) and another reaction with a second binding partner (for example, the same or a different reactive immunological species having affinity for the analyte) that is not bound directly to the surface and that is coupled to a signal-generating label. In this example of a sandwich assay, the presence of the analyte is indicated by the presence of the signal at the location upon which the first binding partner is bound or coated. As the foregoing examples illustrate, many assays, both competitive and noncompetitive, involve the binding of analytes with molecules that are bound or affixed to, or contained within, a solid surface or object.

Many assays indicate the presence or concentration of an analyte or suspected analyte through the generation or suppression of a signal on a surface or in a zone on that surface. The presence, location, or type of signal is not critical to the invention, and any type of assay may be used, regardless of the absence or presence of a signal, or the type of signal involved. Some examples of signals used in assays include those that result from the labeling of a molecule with another molecule, a moiety, or an object that will cause the labeled molecule to exhibit a detectable effect or property. Examples of suitable labels include but are not limited to: enzymes capable of reacting to produce a colored reaction product, such as horseradish peroxidase and alkaline phosphatase; radioactive molecules; molecules capable of producing detectable light such as bioluminescence, chemiluminescence, phosphorescence and fluorescence; radioactive labels; optical density; impedance; electrochemiluminence (ECL); and particles that produce a color change or other visually detectable signal, such as carbon black, colored latex beads or colloidal gold particles.

The signal is then used to determine the presence or absence of the labeled molecule at specific locations or zones on a surface or object. For example, in some "sandwich assay" embodiments, the label is attached to a binding partner for the analyte. Because the analyte or suspected analyte is bound by both the labeled molecule and another, immobilized, binding partner, the label also becomes immobilized, so that the presence of analyte or suspected analyte in the sample is indicated by the existence of the signal in the location or zone in which the immobilized binding partner is located.

In some "competitive assay" embodiments, the label is attached to a binding partner for the immobilized substance. Because the analyte and the labeled molecule compete to bind with the immobilized substance, the presence of the analyte decreases the strength of the signal in the location or zone containing immobilized substance.

In some embodiments involving a test strip, the object is a chromatographic strip having a length and a narrow width and being capable of conveying fluids in a fluid flow direction generally parallel to the length of the strip. In some embodiments, the binding assay is an immunoassay test using a double antibody sandwich format. The in some embodiments contains at least three zones. For example, in some embodiments an antibody specific for an analyte such as $E.\ coli$ O157 is sprayed and immobilized in a zone that forms a line on the surface of a membrane comprising a "test line." A second antibody reagent, also having an affinity the $E.\ coli$ O157 and labeled with a colloidal gold, is contained within a reagent pad upstream from the test line on the membrane. Sample is applied at a filter pad in a location upstream of both the reagent pad and the test line. After application, the sample moves by capillary action from the filter pad into the antibody-gold pad, the antibody-gold reagent binds $E.\ coli$ and moves with the liquid sample into the test membrane. The sample passes through the test line where the immobilized $E.\ coli$ antibody captures the $E.\ coli$-antibody-gold complex, causing the formation of an antibody-$E.\ Coli$ "sandwich" and development of red color at the test line. Sandwiches are not formed in the absence of the $E.\ coli$, resulting in no red color development at the test line. Reagents immobilized in a control line located downstream of the test line capture excess gold reagent passing through the test line. The presence of red color at the control line indicates that the strip test flowed correctly. Therefore, the presence of only one line (control line) on the membrane indicates a "negative" sample (that is, no analyte) and the presence of two lines (test line and control line) indicates a "positive" sample (that is, analyte is present). The test line contains the concentrated substance. Again, this is just one example of some embodiments, and the invention is not limited to it.

In some embodiments involving competitive assays and a test strip, the strip includes the following zones: (1) a sample contact zone where sample composition suspected of containing an analyte is contacted with the strip; (2) a labeled anti-first substance zone disposed at, or downstream from the sample contact zone comprising diffusible labeled anti-first substance; (3) a first substance zone disposed at, or downstream from the labeled anti-first substance zone comprising diffusible unlabeled first substance in an amount sufficient to bind approximately at least all of the labeled anti-first substance; (4) a trapping zone on the strip at, or downstream from, the first substance zone comprising immobilized second substance (in which the first and second substances are binding partners to each other) in an amount sufficient to bind at least a sufficient amount of the unlabeled first substance to bind substantially all of the labeled anti-first substance; and (5) a detection zone on the strip at a downstream location from the trapping zone comprising an immobilized binding moiety specific for the first substance. The analyte for which the test is performed (or a portion of the analyte that shows the desired affinity) may be either the first substance or the second binding substance. The substance that is not the analyte or portion thereof is a binding partner for the analyte. In the absence of analyte in a sample, all of the label is trapped prior to the detection zone, yielding a negative result. The presence of analyte in the sample produces a positive signal due to the presence of label in the detecting zone. The strength of the signal increases proportionately as the amount of analyte in the sample increases. Thus, the detection zone contains the concentrated substance.

The embodiments in the previous paragraph have many variations. One variation entails combining both diffusible assay components with the sample prior to application to the strip, and using a strip that includes zones (1), (4), and (5) set forth in the previous paragraph, and need not include zones (2) and (3). In this variation, the sample to be tested is combined with diffusible labeled anti-first substance and diffusible unlabeled first substance to form a sample-assay component mixture, and the sample-assay component mixture is applied to the sample contact zone, and the presence of label in the detection zone is detected. Another variation involves a strip that includes zones (1), (2), (4), and (5) set forth in the previous paragraph, and need not include zone (3). In this variation the sample to be tested is combined with diffusible unlabeled first substance to form a sample-assay component mixture prior to applying the mixture to the sample contact zone. Yet another variation involves a strip that includes zones (1), (3), (4), and (5) set forth in the previous paragraph, and need not include zone (2). In this variation, the sample to be tested is combined with diffusible labeled anti-first substance to form a sample-assay component mixture, the sample-assay component mixture is applied to the sample contact zone, and the presence of label in the detection zone is detected. Again, in each of these variations, in the absence of analyte in a sample, all of the label is trapped prior to the detection zone, yielding a negative result. The presence of analyte in the sample produces a positive signal due to the presence of label in the detecting zone. The strength of the signal increases proportionately as the amount of analyte in the sample increases. In all variations of this embodiment, the existence of a positive signal in the detection zone indicates that some analyte (or suspected analyte) has been immobilized in both zones (4) and (5). However, it also indicates that the substance that shares the same binding moiety as the analyte has also been trapped in both zones. Thus, in some uses this type of test strip is used in connection with methods of isolating or concentrating suspected analyte for the purposes of confirming the identity of a suspected analyte, it may be appropriate in some embodiments to take measures to assure that the two substances that are binding partners do not perturb or interfere with the accuracy of the confirmation. For example in some embodiments in which the analyte is a specific bacteria or other pathogen, the binding partner that shares the same binding affinity as the bacteria can be a cell or cell wall fragments or other molecules from the pathogen that to which the other binding partner has an affinity.

Any binding assay may be used in the present invention. Many binding assays are known in the art and many are commercially available. For assays in which the analyte is a pathogenic bacteria, examples of such assays include, but are not limited to, RAPIDCHEK *E. coli* O157 tests available from Strategic Diagnostics, Inc., Newark, Del. (referred to as "SDI" herein); VIP *E. coli* tests available from BioControl Systems Inc., Bellevue, Wash.; REVEAL tests from Neogen Corporation, Lansing, Mich.; IMMUNOCARD STAT! *E. coli* O157:H7 from Meridian Diagnostics, Inc., Cincinnati, Ohio; OXOID *Listeria* Rapid Test from Oxoid Limited, Hampshire, England; VIDAS ECO from bio Meriux Vitek. Inc., Hazelwood, Mo.; and Unique Salmonella Assay from Tecra International Pty Ltd., Chatswood, Australia.

The foregoing are merely examples of some of the binding assays with which the methods, devices, and kits of the invention can be used, and are not intended to be limiting. Any type of binding assay may be used in or combined with the methods, devices, and kits of the present invention.

Methods of Concentration and Other Methods That Include a Concentrating Step

The invention includes methods for concentrating analytes or suspected analytes and methods of analysis that include the concentration method followed by further analysis of the concentrated analyte or suspected analyte. In some embodiments, the sole process of immobilizing analytes or suspected analytes on a surface in a binding assay, then removing the immobilized analyte from the surface or separating the surface from other parts of the binding assay, serves to concentrate the analyte for purposes of practicing the methods of the invention.

In some embodiments, the concentrating method or concentrating step of a method includes further processes undertaken to increase analyte concentration. The immobilized analyte is placed, for example, in conditions effective to cause proliferation, replication, or reproduction of the substance, or any other process that causes the amount or the concentration of the substance to increase. Any conditions that will allow such processes to proceed can be used. In some embodiments in which the substance is an organism, the methods include placing the microbes immobilized through the binding assay in an environment that will allow reproduction of the organism. Examples include, but are not limited to, agars, broths, enriched media, animal models, and other environments used to culture the growth of organisms in vitro or in vivo. In some embodiments, the environments include those with high degrees of selectivity for the growth of one or more specific taxa, strains, classes, or types of organisms, environments with little or no selectivity, and degrees of selectivity anywhere between these extremes. In some embodiments in which the substance is a molecule or group of molecules, examples of such conditions include those effective to cause replication of the molecule.

The types of environments used to concentrate analytes or suspected analytes depend upon the type of analytes or suspected analytes involved. Some examples of selective agars useful in concentrating *E. coli* O157 bacteria include, but are not limited to, Cefixie-Potassium Tellurite Sorbitol MacConkey agar (referred to herein as "CT-SMAC"); available from Becton, Dickinson and Company, Sparks, Md. and RAINBOW Agar O157, available from Biolog Inc., Hayward, Calif. Some examples of selective agars useful in concentrating *Salmonella* bacteria include ASAP *Salmonella* plates (available from AES Laboratoire, Combourg, France) as well as Xylose Lysine Deoxycholate (XLD) plates, XL4T agar, Hektoen Enteric (HE) agar, and Brilliant Green Sulfadiazine (BGS) plates, (each available from Becton, Dickinson and Company, Sparks, Md.). Other examples of agars for bacteria include Eosin Methylene Blue (referred to herein as "EMB"), Phenol Red Sorbitol Agar, Blood Agar, and Luria Bertani Agar (referred to herein as "LB"), all available from Becton, Dickinson and Company, Sparks, Md. Examples of selective agars useful in concentrating *Listeria* bacteria include, but are not limited to ALOA *Listeria monocytogenes* plates (available from AES Laboratoire, Combourg, France) as well as the OXFORD *Listeria* agar and the modified OXFORD Listeria agar (both available from Becton Dickinson, Sparks, Md.). Examples of broths or other media that can be used include, but are not limited to, RAPIDCHEK *E. coli* O157 broth available from Strategic Diagnostics, Inc., Newark, Del., as well as Brain Heart Infusion (BHI) broth (available from Becton, Dickinson and Company, Sparks, Md.); Modified EC medium (available from Becton, Dickinson and Company, Sparks, Md.); buffered *Listeria* enrichment broth (available from Becton, Dickinson and Company, Sparks, Md.); University of Vermont broth (available from Becton, Dickinson and Company, Sparks, Md.) and Fraser broth (available from Becton Dickinson, Sparks, Md.) also be used with similar procedures. The listing of examples of agars and media for bacteria is not limiting, and any environment that concentrates any analyte or suspected analyte is within the scope of the invention.

In some embodiments involving bacteria or other organisms, selective agars and media are used to promote selective growth of specific organisms. Selective media promote growth of one or more specific taxa, strains, or groups of organisms to a greater extent than others, or in combination with inhibition of others.

Any method can be used for transferring the bound analyte or suspected analyte from the test device upon which it is bound to an environment or medium in which it will be further concentrated. In some embodiments, the surface to which the analyte is bound is streaked upon a plate of agar or other solid medium. In some embodiments, the surface is immersed within or placed in contact with a liquid broth, medium, or other liquid in which concentration will occur. In embodiments involving surfaces containing multiple zones such that only certain portions of the surface contain immobilized suspected analyte, such portions are optionally cut, scraped, washed, rubbed, lifted, abraded, or otherwise separated from the remainder of the surface for placement in contact with an environment and medium. In some embodiments, the surface or portion thereof is placed in an enriching medium for a period of time, then streaked upon agar. In some embodiments, the surface is processed prior to placement in the medium or environment for the purposes of rendering the suspected analyte more amenable to concentration. For example, in some embodiments surfaces are cut into smaller pieces, washed in a nutrient media, or treated with an agent to weaken or to break the bond holding the analyte to the surface, or a combination of the foregoing.

In some embodiments involving substances that are organisms, placement of the suspected analyte in a medium may result in the growth of more than one substance. In these embodiments, additional steps are optionally used to isolate or to obtain a pure culture of a specific organism. For example, in some embodiments using agar as a medium, the method optionally includes additional steps of observing colonies growing in agar, locating a colony that is isolated (that is, not overlapping with a colony that appears to be of a different strain, species, or type), and transferring a portion of that colony to another medium. Multiple successive platings or transfers to additional media are used in some embodiments to further concentrate a target substance. In some embodiments involving substances that are organisms, similarity in the appearance and morphology of isolated colonies pose obstacles in identifying the organism of interest from plated cultures. For example, on some agar plates colonies of some types of *Enterococcus* and *Bacillus* have morphology that is similar to that of some colonies of *Listeria*. In these embodiments, colonies are optionally subjected to further testing (for example, a repeat of the binding assay) to verify that they contain the substance that initially produced the positive result in the binding assay.

Methods of Isolation

The invention further includes methods for isolating analytes. The methods of concentration discussed above can also serve to isolate specific analytes that have a given binding affinity. In some embodiments, the analyte's affinity for the binding partner in an assay is sufficient to separate a specific analyte from other substances in a sample. In other embodiments, additional steps of concentration are selected to promote proliferation, reproduction, or replication of only specific types or classes of substances. In some embodiments, multiple successive platings are used and are optionally accompanied by measures taken to isolate non-overlapping colonies of a specific type.

Methods of Characterization or Identification of a Substance

The invention further includes methods of characterizing or identifying a substance that is bound by a binding assay. These methods begin with the concentrating methods outlined above. Additional analysis is then performed on the concentrated substances to determine their identity.

In some embodiments, the identification process involves placing the suspected analyte under conditions effective to indicate its identity. In these embodiments, the only concentrating done is the concentration that occurs as part of the binding assay and separating the bound substance from the surface or, alternatively, separating the surface from the remainder of the test assay articles. In some embodiments, bound bacteria is streaked directly upon several agar plates of high selectivity or placed in another highly selective medium. Because of the degree of selectivity of the medium, the subsequent growth (or absence thereof) of a colony alone can provide a basis for identifying a substance. In some embodiments, however, the failure to grow upon highly selective media is not necessarily a definitive indication.

In some embodiments, additional testing is undertaken to more completely characterize the bound substance. In some embodiments, the testing is preceded by the isolation methods to assure that the substance is pure. For example, some embodiments use successive platings of bacteria in which non-overlapping, isolated cultures are identified and transferred to additional plates for further growth prior to characterization.

Any method or combination of methods for characterizing or identifying the analytes may be used. Examples of methods used in some embodiments involving bacteria as analytes include, but are not limited to: strip test binding assays similar to those discussed herein; agglutination assays such as the REMEL *E. coli* O157 Latex (available from REMEL, Inc., Lenexa, Kans.), REMEL *E. coli* H7 Latex (available from REMEL, Inc., Lenexa, Kans.), and the REMEL Salmonella Latex (available from REMEL, Inc., Lenexa, Kans.); test characterization kits such as the REMEL MicroID system (available from REMEL, Inc., Lenexa, Kans.) and the bio Meriux api20E system (available from bio Meriux Vitek. Inc., Hazelwood, Mo.); DNA polymerase chain reaction tests such as the BAX *E. coli* O157:H7 test (available from DuPont Qualicon Inc., Wilmington, Del.); motility tests for determining the presence and structure of types of flagella such as the H7 flagellates; and toxicology tests that identify the characteristics of toxins produced by a bacteria. Tests performed by outside services such as the H 1-58 Serotyping performed by the *E. coli* Reference Center (Department of Veterinary Science at The Pennsylvania State University, University Park, Pa.) and the H Serology test, (also performed by the *E. coli* Reference Center), are also used for this purpose in some embodiments.

In some embodiments, a substance is first isolated or concentrated by a binding assay for which the substance indicates a positive result for a given analyte. The substance is thus a suspected analyte. The substance that is bound by the binding assay is then placed in conditions that are effective to cause proliferation, reproduction, or replication of the bound substance. Optionally, successive steps of concentrating and isolating methods are performed to obtain a sample that is pure or that has a sufficient high concentration of a substance to allow testing to characterize or to identify the substance.

In some embodiments, a Lateral Flow Device test (for example, the RAPIDCHEK *E. coli* O157 available from Strategic Diagnostics, Inc., Newark, Del.) is conducted. The membrane in the test strip is accessed by removing the cassette and the clear cover from the strip membrane. A piece of membrane is then cut around the test line using sterile forceps and scissors. In some of these embodiments, the cut membrane is placed on a selective agar plate (test line face down), then streaked along the agar surface for about 1 inch. The streak is then spread upon the agar with a sterile loop to form a colony or colonies. In some of these embodiments, *E. coli* O157 is confirmed by directly streaking the membrane on both Rainbow Agar and CT-SMAC. After streaking, the excised membrane is placed in an Eppendorf tube containing 1 ml RAPIDCHEK *E. coli* broth (available from Strategic Diagnostics Laboratories, Inc., Newark, Del.) and incubated at 42° C. for 2-6 hours. The membrane is then streaked again on selective agar plates (i.e., Rainbow agar and CT-SMAC). All streaked plates are incubated at an appropriate incubation temperature for 24 hours and examined for typical colonies. *E. coli* O157 colonies appear to be dark blue on RAINBOW agar, colorless on CT-SMAC. Optionally, the colony is further tested by moving a portion of the colony into 150-500 microliters of media or peptone water, and running a second Lateral Flow Test on the result. Additional confirmation procedures are used as appropriate.

Stability and Storage of Bound Samples

In many cases the use of substances immobilized by binding assays, including substances that are cells or organisms, provides conditions in which bound substances can be stored for some time. In some embodiments, immobilized suspected analyte bound to a test strip (for example a RAPIDCHEK *E. coli* O157 test) are left to stand for a period of time after testing without any efforts to preserve the moisture, nutrients, or other conditions that allow growth of the organisms. Subsequent efforts to isolate live *E. coli* O157 cultures are nevertheless successful. In some embodiments, the period of standing is greater than zero and up to about 24 hours. In some embodiments, the period of standing is at about 24 to about 48 hours. In some embodiments, the period of standing is about 48 hours to about five days. In some embodiments, the period of standing is at least about five days. In some embodiments, the period of standing is about four days to about five days. This durability creates great flexibility for users that wish to confirm or identify a suspected analyte using an outside laboratory because it allows users to ship test strips offsite. In some embodiments, longer shelf times are possible where measures are taken to keep the test strip moist. Examples of such measure would be addition of peptone water or other moisturizing medium.

Kits and Devices for Performing the Methods of the Invention

The invention also includes kits containing the materials for performing the methods of the present invention and articles and reagents to be used in performing the methods. In some embodiments, the kits include equipment and materials for performing concentration, and optionally for performing isolation, confirmation or both. Examples of such materials include, but are not limited to, media in which concentration occurs and materials for performing confirmation tests and other tests for characterization or identification of the analytes or suspected analyte. Such tests include, but are not limited to, any tests for identification or characterization provided herein. Some embodiments combine the materials for performing these processes with the materials and equipment for performing a binding assay. In some embodiments, the kit includes a binding assay using a test strip, such as the commercially available binding assays listed above. Such assays include, in some embodiments, the test strips, instructions for use and for interpreting the results, and materials to assist in preparing samples (such as, for example, materials for culturing bacteria in a food sample). In some embodiments, the articles have a structure that will allow easy removal of the zone containing the immobilized analyte or suspected analyte from the remainder of the article or removal of the bound substance from that zone or surface. In some embodiments, a test strip has a physical structure and distribution of zones similar to that in the RAPIDCHEK *E. coli* O157 available from Strategic Diagnostics, Inc., (Newark, Del.), but modified to add structural features that will allow easy removal of the zone containing the immobilized analyte or suspected analyte. Such modifications can include but are not limited to openings in the plastic cover that will allow access to the desired zone for removal and structural features such as perforations in the test pad to facilitate separation of the zone from the other portions of the test pad.

EXAMPLES

Many of the examples below use the RAPIDCHEK lateral flow test (Strategic Diagnostics, Inc., Newark, Del.). This binding immunoassay uses a double antibody sandwich format. The strip contains at least three zones. Antibodies specific for a bacteria (for example, for *E. coli* O157) are sprayed and immobilized in a zone that forms a line on the surface of a membrane referred to as a "test line." A second antibody reagent, also recognizing the bacteria and labeled with a colloidal gold, is contained within a reagent pad upstream from the test line on the membrane. As the sample moves by capillary action from the filter pad into the antibody-gold pad, the antibody-gold reagent specifically binds the bacteria and moves with the liquid sample into the test membrane. The sample passes through the test line where the immobilized bacteria antibody captures the bacteria-antibody-gold complex, causing the formation of an antibody-bacteria "sandwich" and development of red color at the test line. Antibody-bacteria sandwiches are not formed in the absence of the bacteria, resulting in no red color development at the test line. Reagents immobilized at the control line capture excess gold reagent passing through the test line. The presence of red color at the control line indicates that the strip test flowed correctly. Therefore, the presence of only one line (control line) on the membrane indicates a negative sample and the presence of two lines indicates a positive sample.

The RAPIDCHEK procedures for food samples include an enrichment step prior to testing. The RAPIDCHEK kits and many similar kits provide instructions for enrichment procedures. The purpose of enrichment is to increase the concentration or amount of any pathogens in the sample to aid in detection. Examples of enrichment methods include but are not limited to: enriching the sample in RAPIDCHEK broth for 8 hours; enriching the sample in RAPIDCHEK broth for 18 hours; and enriching the sample in Modified EC medium for 20 hours.

EXAMPLE 1

Concentration, Isolation, and Identification of an *E. coli* O157 Non-H7 Strain

A beef sample weighing 25 grams, showing a positive result on the RAPIDCHEK *E. coli* O157 lateral flow test, was enriched in 225 milliliters of RAPIDCHEK *E. coli* O157 broth for 8 hours as stated in the manufacturer's instructions. (This broth is also available from Strategic Diagnostics, Inc.). This culture was streaked on CT-SMAC agar and RAINBOW agar O157 (Biolog Inc., Hayward, Calif.), both of which are highly selective for *E. coli* O157. The plates were incubated at 37° C. for 24 hours, and examined for typical *E. coli* O157 colonies. None were observed. One ml of the original culture was transferred into 10 ml RAPIDCHEK broth, incubated at 42° C. for 8 hours, and tested on a RAPIDCHEK strip again. This reading was a strong positive, providing a color card reading of 10 units on a scale of 1-11 units with a higher number of units representing a stronger signal. This culture was streaked again on CT-SMAC and RAINBOW Agar O157, incubated overnight, and no typical colony was found. The same culture was transferred to Modified EC Medium (available from Becton, Dickinson and Company, Sparks, Md.) for 20 hours of growth at 37° C. The resulting cultures were streaked on Rainbow Agar and CT-SMAC plates, and the plates were incubated at 37° C. overnight. The plates were examined, and no typical colony was found.

A test line from a RAPIDCHEK test strip used to test an 8 hour RAPIDCHEK test broth was excised from the test strip using a pair of sterile scissors and forceps, and a membrane with a size of about 5 mm×5 mm was obtained. Using the same forceps to hold this membrane, the test line was streaked upon various agar plates, including CT-SMAC, RAINBOW agar, EMB, Blood Agar and LB Agar. All plates were incubated at 37° C. for 24 hrs. Isolated, non-overlapping colonies from each plate were each transferred into 150 microliters of peptone water and mixed well. These solutions were then subjected to RAPIDCHEK *E. coli* O157 strip tests. One isolated colony from an EMB agar plate (a partially selective medium that tends to select coliforms) was identified to be a strong positive on the test (color card reading higher than 9). This colony was re-streaked to various plates for additional isolation from contamination. Results are provided in Table 1.

The pure isolate of this colony was identified to be *E. coli* using api20E identification system (available from bio Meriux Vitek. Inc., Hazelwood, Mo.) as well as MicroID System available from REMEL, Inc. Lenexa, Kans. Additional characterization of this isolate was obtained further plating and testing. Motility testing was performed using a Motility Agar tube (available from Becton, Dickinson and Company, Sparks, Md.). The culture was inoculated with a sterile needle, incubated at 37° C. overnight. The growth pattern of the culture was examined and evaluated as "motility positive." Results of all characterizations are presented in Table 1. Results indicate that the strain is an *E. coli* O157 non-H7, and that it does not grow well on CT-SMAC and RAINBOW agar. The strain is sorbitol positive.

TABLE 1

Additional Analysis of *E. coli* O157 non-H7 strain from Beef Sample after Isolation of Colony on EMB Agar

| No. | Test | Result | Comments |
| --- | --- | --- | --- |
| 1 | Enriched the cut membrane in RAPIDCHEK broth | Positive | Difficult to isolate |
| 2 | Re-streak the isolated, non-overlapping colony from EMB to various agar plates | | A single colony was isolated |
| 2a | LB Agar, Miller (for total count, BD, Sparks, MD) | Growth | Clear shiny colony, good growth |
| 2b | Blood agar (for total count) (REMEL, Inc. Lenexa, KS) | Growth | clear shiny colony with gray center |
| 2c | Phenol Red Sorbitol (for sorbitol utilization) (BD, Sparks, MD) | Growth | yellow, clear colony |
| 2d | EMB (for coliform) (BD, Sparks, MD) | Growth | pink, black center, metallic sheen |
| 2e | XLD (selective for *Salmonella*) (BD, Sparks, MD) | Growth | fair growth, yellow and rough colonies |
| 2f | BGS (Selective for *Salmonella*) (BD, Sparks, MD) | Inhibited | Poor growth, gray |
| 2g | CT-SMAC (Selective for *E. coli* O157) | Inhibited | Poor growth, purple |
| 2h | RAINBOW agar (for *E. coli* O157) | Inhibited | Poor growth, gray |
| 2i | AES *Salmonella* ASAP plate (AES Laboratoire, Combourg, France) | Growth | Fair growth, colorless colonies |
| 3 | REVEAL test (Neogen Corp,, Lansing, MI) with isolated colony | Positive | Very strong signal |
| 4 | REMEL *E. coli* O157 Latex (REMEL Inc., Lenexa, KS) (agglutination assay for *E. coli* O157) | Positive | O157 strain |
| 5 | REMEL *E. coli* H7 Latex (REMEL Inc. Lenexa, KS) (agglutination assay presence of H7 flagella) | Negative | No H7 flagella present |
| 6 | REMEL *Salmonella* Latex (REMEL Inc., Lenexa, KS) (agglutination assay) | Negative | No *Salmonella* present |
| 7 | REMEL MicroID system (REMEL Inc., Lenexa, KS) | *E. coli* | Test results give confirmation based on multiple characterizations |
| 8 | Bio Meriux api20E system (bio Meriux Vitek. Inc., Hazelwood, MO) Example results from bioMeriux api20E | *E. coli* | Test results give confirmation based on multiple characterizations |
| 8a | Lysine decarboxylase (LDC) | Positive | O157:H7 and *Citrobacter* all positive |
| 8b | Citrate utilization | Negative | All Citrobacter positive |
| 8c | Hydrogen sulfide production | Negative | *C. freundii* and most *Salmonella* positive |
| 8d | Indole production | Positive | Typical *E. coli* positive |
| 8e | Voges-Proskauer reaction | Negative | Typical *E. coli* negative |
| 8f | Ornithine decarboxylase (ODC) | Negative | O157:H7 positive |
| 8g | Sorbitol utilization | Positive | O157:H7 negative for sorbitol |
| 8h | Rhamnose utilization | Negative | O157:H7 positive for Rhamnose |
| 8i | Sucrose utilization | Negative | O157:H7 positive for sucrose |
| 9 | Neogen's Reveal test (Neogen, Lansing, MI) with isolated colony | Positive | Very strong signal |
| 10 | REMEL *E. coli* O157 Latex (REMEL Inc., Lenexa, KS) | Positive | O157 strain |
| 11 | REMEL *E. coli* H7 Latex (REMEL Inc., Lenexa, KS) | Negative | Not H7 |
| 12 | REMEL *Salmonella* Latex (REMEL Inc., Lenexa, KS) | Negative | not *Salmonella* |
| 13 | REMEL MicroID system (REMEL Inc., Lenexa, KS) | *E. coli* | Excellent identification |
| 14 | Motility test | Positive | This is an O157 non-H7strain |
| 15 | BioControl VIP *E. coli* O157 Test (BioControl Systems Inc., Bellevue, WA) | Positive | This is an O157 strain |
| 16 | Qualicon BAX *E. coli* O157:H7 test (Wilmington, DE) performed by Siliker Lab (Homewood, IL) | Negative | This is not an H7 strain |
| 17 | H 1-58 Serotyping as by *E. coli* Reference Center (PA State University, PA) | All Negative | This is not any one of H1-58 strains. |

TABLE 1-continued

Additional Analysis of *E. coli* O157 non-H7 strain from
Beef Sample after Isolation of Colony on EMB Agar

| No. | Test | Result | Comments |
| --- | --- | --- | --- |
| 18 | Toxicity test (characterization of toxins produced) Performed by *E. coli* Reference Center (PennState University, University Park, PA) | Negative | Heat labile, stable a, b, shiga like 1,2 |

EXAMPLE 2

Identification an *E. coli* O157 Strain Using Selective Media

A beef sample was used to prepare an 8 hour RAPID-CHEK broth using the instructions accompanying the commercially available broth. The broth was tested with a RAPIDCHEK *E. coli* O157 test and was shown to be positive. The test line from the RAPIDCHEK test strip was cut using a pair of sterile scissors and forceps, and a membrane with a size of about 5 mm×5 mm was obtained. Using the same forceps to hold this membrane, this culture was streaked on CT-SMAC and RAINBOW Agar O157, both of which are highly selective for *E. coli* O157. The plates were incubated at 37° C. for 24 hours, and examined for typical *E. Coli* O157 colonies. Typical *E. coli* O157 colonies were observed on both types of agar confirming the results of the RAPIDCHEK test.

EXAMPLE 3

Isolation of *Salmonella* Crossreactor Strains

In this experiment, a test strip for *Salmonella* was used to evaluate samples of raw chicken or raw ground beef. The strip test was similar to the RAPIDCHEK *E. coli* O157 test except that it used polyclonal antibodies having a binding affinity for *Salmonella* rather than antibodies having an affinity for *E. coli*. Raw ground beef samples were obtained from a local supermarket, and measured into 25 gram samples. A total of 50 samples were prepared for each. 45 samples were spiked with 1-10 cells of *Salmonella*, with the other five samples serving as negative control (un-spiked). Samples and controls were then enriched in the RAPID-CHEK *Salmonella* enrichment media for 24 hr, then tested on the strips. All 5 negative control samples indicated positive on the strip tests. However, none of the negative controls were confirmed to be typical *Salmonella* by streaking the cultures on *Salmonella* selective agar plates, such as AES ASAP *Salmonella* plates, Xylose Lysine Deoxycholate (XLD) plates and Brilliant Green Sulfadiazine (BGS) plates.

The test line was excised from the strip using the procedures described in Example 1. The exised membranes were streaked directly to XLD and BGS plates, incubated at 37° C. for 24 hours. Single isolated, non-overlapping colonies were tested again on the *Salmonella* strips. A total of 9 cultures were isolated and they were identified using the bio Meriux api20E system (available from bio Meriux Vitek. Inc., Hazelwood, Mo.) as strains that crossreact with the Salmonella antibody used in the strip. One additional strain of Aeromonas was isolated from a chicken sample. These strains as listed in Table 2 were used for purification of the antibody by cross absorption with live cells. Cross absorption involved suspending some of the cells of the strains in Table 2 along with a serum containing the polyclonal antibodies originally used to make the test strip and incubating to allow binding of the crossreactive antibodies to the cells. Subsequently removing the cells from the serum caused removal or reduction in quantity of the bound nonspecific antibodies, thus providing a more specific polyclonal antiserum. that was used in preparing additional test strips having diminished crossreactivity with the strains in Table 2.

TABLE 2

Isolation of *Salmonella* Cross Reactor Strains

| Isolate No. | Identification | Source |
| --- | --- | --- |
| 1 | *Citrobacter freundii*, H$_2$S positive | Beef |
| 2 | *Enterobacter cloacae* | Beef |
| 3 | *Citrobacter freundii*, H$_2$S positive | Beef |
| 4 | *Citrobacter freundii*, H$_2$S positive | Beef |
| 5 | *Citrobacter freundii* | Beef |
| 6 | *Citrobacter freundii* | Beef |
| 7 | *Citrobacter freundii* | Beef |
| 8 | *Aeromonas hydrophila* | Chicken |
| 9 | *Klebsiella pneumonia* | Beef |
| 10 | *Aeromonas hydrophila* | Beef |

EXAMPLE 4

Rapid Check of the Purity of Known Culture

In this study, a culture of *Listeria monocytogenes* ATCC 19115 was subjected to a *Salmonella* test strip assay. A strong positive result was found with this culture. The test line was excised and directly streaked on various agar plates, including XLD, BGS, and AES ASAP *Salmonella* plates, and ALOA *Listeria monocytogenes* plates (AES, Combourg, France). All plates were incubated at 37° C. for 24 hrs. Two types of colonies were found from the plates and one of them was identified as *Salmonella* spp. This confirmed that the original culture of *L. monocytogenes* was contaminated with *Salmonella* strain.

EXAMPLE 5

Stability of Bacteria on the Strip After Test

The goal of this experiment was to examine the stability of the bacteria on the test strip after the assay. Two 25 gram ground beef samples were incubated with 225 ml each of RAPIDCHEK broth at 42° C. for 20 hrs, one sample was spiked with 10 *E. coli* O157:H7 cells, and another was used as a control. The *E. coli* O157:H7 cells were of a strain known to grow on both CT-SMAC and RAINBOW agar. After enrichment, the samples were tested on RAPIDCHEK E. coli O157 strips by loading 150 microliter samples on a strip. The control sample was negative on the strip, and the spiked sample was positive and had a color card reading of 7.0. A portion of the spiked sample was diluted 10× in the negative sample, and tested again, which gave a positive result with a card reading of 2.0 units. A total of seven samples from each of these three groups, (negative control, diluted spiked, and spiked samples, designated as C0, C2, and C7, respectively) were subjected to a RAPIDCHEK E. coli O157 strip again with 7 replicates each, and after the test, the strips were left to dry on the bench for a period of up to 15 days. At the following time points, day 0 (fresh), 1, 2, 5, 15, a strip was processed by opening the strip, and excising the test line using the procedures set forth in EXAMPLE 1. The excised test lines were directly streaked on the selective agar plates, i.e., CT-SMAC and/or RAIN-BOW agar plates. Each excised membrane in the tests was also incubated in 1 ml Brain Heart Infusion (BHI) broth or 1 ml RAPIDCHEK broth at 42° C. for 2-24 hrs after direct streaking, followed by streaking the original membrane again on selective agar, or both to confirm the presence of E. coli O157.

As shown in the following Table 3, the E. coli O157 can be confirmed from both samples of C2 and C7 on the strips 48 hours after the test was run.

TABLE 3

Stability of Bacteria on the Strip after Test

| Sample | E. coli O157 (cfu/ml) | Confirmation from the Strip | | | | |
|---|---|---|---|---|---|---|
| | | Day 0 | Day 1 | Day 2 | Day 5 | Day 15 |
| C0 | 0 | Negative | Negative | Negative | Negative | Negative |
| C2 | $4 \times 10^4$ | Positive | Positive | Positive | Negative | Negative |
| C7 | $4 \times 10^5$ | Positive | Positive | Positive | Positive | Negative |

This study indicated that after the test strip is used, the strip is stable and can be sent to an offsite lab for accurate confirmation. There is no need to send liquid samples, though it may aid durability to maintain the strip in a moist environment during the transportation. This is an advantage for small labs, who do not routinely do the confirmation work by themselves.

EXAMPLE 6

Efficiency of Directly Streaking Membrane on Selective Agar Plates for Confirmation This experiment compared confirmation methods that include directly streaking an excised membrane on selective agar plates with methods that involve incubating the excised membranes. Samples of the C2 and C7 cultures prepared in EXAMPLE 5 were used. Each sample was subjected to a RAPIDCHEK E. coli O157 test. After the test was completed, the strips were left on a bench for 48 hours with no source of moisture. The test line was excised from each strip and directly streaked on RAINBOW agar and CT-SMAC agar. After streaking, the membranes were incubated with 1 milliliter of RAPIDCHEK E. coli O157 broth at 42° C. for a period of up to 24 hours. Membranes were streaked after incubation for 2 hours, 3 hours, 6 hours, or 24 hours. All streaked plates were incubated at 37° C. for 24 hrs and examined for typical E. coli O157 colonies. Results are presented in Table 4 and Table 5 below.

TABLE 4

Streaking Membrane after Additional Incubation

| Sample ID | E. coli O157 (cfu/ml) | Directly Streaked | Streaked after 24 hr enrichment |
|---|---|---|---|
| C0 | 0 | Negative | Negative |
| C2 | $4 \times 10^4$ | Negative on Rainbow, positive on CT-SMAC | Positive on both Rainbow and CT-SMAC |
| C7 | $4 \times 10^5$ | Positive | Positive |

TABLE 5

Sample streaked after the test was run and held at room temperature for 48 hrs

| Sample ID | E. coli O157 (cfu/ml) | Directly Streaked | Streaked after 3 hours incubation | Streaked after 6 hours incubation |
|---|---|---|---|---|
| C0 | 0 | Negative | Negative | Negative |
| C2 | $4 \times 10^4$ | Negative | Positive | Positive |
| C7 | $4 \times 10^5$ | Negative | Positive | Positive |

The method described in this Example is useful as a combination of immunocapture and enrichment of pathogens for various pathogen tests. It was observed that streaking the cut membrane yielded negative results in situations in which incubation provided positive results. While not wanting to be bound to a theory, in some embodiments the bound cells may be affected in a way that reduces ability to be streaked or viability or normal function of cells after streaking. Incubating may result in the reproduction of cells whose growth after streaking is not compromised. In addition, the stronger the test line, the easier it is to confirmed the result on selective plates. With a weak positive sample, such as C2, it was more sensitive to streak the membrane after the membrane was incubated in liquid media for another 2 hrs or longer.

EXAMPLE 7

Isolation of Listeria and *Salmonella* Strains

Test strips containing specific antibodies for either *Salmonella* or *Listeria* were used for the detection of each of these organisms in various food and environmental samples after enrichment. For testing ground chicken samples for *Salmonella,* for example, 25 grams of the food samples were mixed with 225 ml of RAPIDCHEK *Salmonella* media (also available from Strategic Diagnostics, Inc.). The sample was then incubated at 42° C. for 5-18 hours. After that, 1 ml of the enriched culture was transferred to 10 ml tetrathionate broth, Hajna (TTH) (available from Becton Dickinson and Company, Microbiology Systems, Sparks, Md.), and further incubated at 42° C. for 19 hours. 150 microliters of the enriched TTH was tested on the RAPIDCHEK *Salmonella* test strip (available from Strategic Diagnostics Inc.,). The observance of a positive signal using the RAPIDCHEK test was indicative of the suspected presence of *Salmonella* in specific samples.

To verify positive results in the samples, the test lines were excised from test strips showing a positive result using the excision procedures described in Example 2 or with a similar excision procedure using sterile excision and handling equipment. The excised test line membrane were each held by sterile forceps and streaked directly on various the BGS and XLT4 selective agar plates. The plates were then examined for typical *Salmonella* colonies. Presence of colonies on either of the selective plates confirmed the identity as *Salmonella*.

For testing the presence of *Listeria,* samples (for example, 25 gram samples of meat) were each incubated in 225 ml of a *Listeria* enrichment broth at 30° C. for 40 hours. Following enrichment, a 150 microliter portion of the broth containing enriched sample was applied to a *Listeria* immunoassay test strip. An observed positive signal indicates the suspected presence of *Listeria* in the sample. The positive test line was excised as described in Example 2, and directly streaked on selective agar plates using the modified OXFORD Listeria agar (available from Becton Dickinson, Sparks, Md.). The plates were incubated for 24-48 hrs at 35° C. Colonies having the appearance of typical *Listeria* colonies were considered further confirmation of the test result.

EXAMPLE 8

Identification of a Listeria Colony Using a Lateral Flow Device

Samples were enriched, tested for *Listeria* using a test strip, then further analyzed using selective media, all using the procedures of EXAMPLE 7. Colonies on some plates overlapped, making morphology difficult to identify due to similarities between *Enterococcus* or *Bacillus* colonies and that of *Listeria*. Further procedures were therefore performed to identify the colonies. Colonies were removed from that plates with a sterile inoculation loop and transferred into 150 ml peptone water. The cell suspension was thoroughly mixed. Each cell suspension was then applied to another *Listeria* test strip similar to those used to test the original samples in EXAMPLE 7. The presence or absence of *Listeria* was then confirmed by a positive reaction or a negative reaction (the negative reaction indicating presence of a different strain such as *Enterococcus* or *Bacillus* rather than *Listeria*). The method herein for *Listeria* characterization is highly specific due to the antibody used in the test strip, and is therefore considered superior to the (nonspecific) blue latex agglutination test often used for confirmation of *Listeria*.

All patents, patent applications, publications and abstracts cited above are incorporated herein by reference in their entirety. To the extent any document incorporated by reference defines a term in a manner inconsistent with a definition provided in this application, the definition provided in this application shall control with respect to terms used in this application. It should be understood that the foregoing relates only to preferred embodiments of the present invention and that numerous modifications or alterations can be made therein without departing from the spirit and the scope of the present invention as defined in the following claims.

What is claimed is:

1. A method for detecting, isolating or purifying a bacteria comprising:
   placing a sample in contact with a device, wherein at least a portion of the device comprises a plurality of zones, wherein at least one zone is a detection zone separable from said plurality of zones and the remainder of the device; wherein the detection zone comprises an immobilized binding partner for a bacteria and wherein binding between the immobilized binding partner and a suspected bacteria causes formation of an optically detectable signal and detection of the signal indicates the presence of a suspected bacteria in the sample;
   separating at least part of the detection zone containing the bound bacteria and immobilized binding partner from said plurality of zones and the remainder of the device; and
   analyzing the separated detection zone containing the bound bacteria and immobilized binding partner without detaching the bound bacteria from the immobilized binding partner to provide information regarding the suspected bacteria.

2. The method of claim 1, wherein the device is a lateral flow device.

3. The method of claim 1, wherein the information identifies the suspected bacteria.

4. The method of claim 1, wherein the information describes one or more characteristics of the suspected bacteria.

5. The method of claim 1, further comprising:
   placing the separated detection zone containing the bound bacteria and immobilized binding partner in conditions effective to cause the quantity of the suspected bacteria to increase.

6. The method of claim 1, wherein analyzing the separated detection zone containing the bound bacteria and immobilized binding partner comprises placing the separated detection zone containing the bound bacteria and immobilized binding partner on or in a selective growth medium in which the bacteria will proliferate if present.

7. The method of claim 1, wherein the method further comprises storing the device without further processing for up to five days after placing the sample in contact with the device and before separating the detection zone containing the bound bacteria and immobilized binding partner from the plurality of zones and the remainder of the device.

8. A kit for performing the method of claim 1, comprising a device; wherein at least a portion of the device comprises a plurality of zones, wherein at least one zone is a detection zone; wherein the, detection zone comprises an immobilized binding partner for a bacteria, wherein the detection zone is separable from the plurality of zones and the remainder of the device and, wherein the separated detection zone is analyzed to provide information regarding the bound bacteria.

9. The method of claim 1, wherein the bacteria further comprises a food or environmental contaminant.

10. The method of claim 1, wherein the bacteria is a pathogen.

11. The method of claim 1, wherein analyzing the separated detection zone containing the bound bacteria and immobilized binding partner to provide information regarding the suspected bacteria comprises analyzing the separated detection zone containing the bound bacteria and immobilized binding partner using a strip test binding assay, an agglutination assay, a DNA polymerase chain reaction test, a motility test, a toxicology test, and serotyping.

12. The method of claim 1, wherein analyzing the separated detection zone containing the bound bacteria and immobilized binding partner to provide information regarding the suspected bacteria comprises analyzing the separated detection zone containing the bound bacteria and immobilized binding partner using a DNA polymerase chain reaction test.

13. The method of claim 1, wherein analyzing the separated detection zone containing the bound bacteria and immobilized binding partner to provide information regarding the suspected bacteria comprises analyzing the separated detection zone containing the bound bacteria and immobilized binding partner using selective media or selective agar plating.

14. The method of claim 1, wherein the bacteria is *Escherichia coli, Salmonella* or *Listeria*.

15. The method of claim 14, wherein the bacteria is *Escherichia* coli O157.

16. The method of claim 1, wherein the optically detectable signal is a light signal.

17. A device for detecting bacteria, wherein at least a portion of the device comprises a plurality of zones, wherein at least one zone is a detection zone separable from said plurality of zones and the remainder of the device; wherein the detection zone comprises an immobilized binding partner for a bacteria and wherein binding between the immobilized binding partner and a suspected bacteria causes formation of an optically detectable signal in the detection zone, and wherein the device comprises structural features that facilitate separation of the detection zone containing the bound bacteria and the immobilized binding partner or a part of the detection zone containing the bound bacteria and the immobilized binding partner from the plurality of zones and the remainder of the device, wherein said separated detection zone or part thereof can be analyzed to provide information regarding the bound bacteria.

18. The device of claim 17, wherein the device is a lateral flow device.

19. The device of claim 17, wherein the optically detectable signal in the detection zone is a light signal.

20. A method for detecting, isolating or concentrating a bacteria by placing a sample containing the bacteria under conditions effective to cause proliferation, replication or reproduction of the bacteria comprising:

placing a sample in contact with a device, wherein at least a portion of the device comprises a plurality of zones, wherein at least one zone is a detection zone capable of being separated from said plurality of zones and the remainder of the device; wherein the detection zone comprises an immobilized binding partner for a bacteria and wherein binding between the immobilized binding partner and a suspected bacteria causes formation of an optically detectable signal and detection of the signal indicates the presence of a suspected bacteria in the sample;

separating at least part of the detection zone containing the bound bacteria and immobilized binding partner from said plurality of zones and the remainder of the device; and subjecting the separated detection zone to conditions effective to cause proliferation, replication or reproduction of the bacteria.

21. The method of claim 20, wherein the device is a lateral flow device.

22. The method of claim 20, wherein the information identifies the suspected bacteria.

23. The method of claim 20, wherein the information describes one or more characteristics of the suspected bacteria.

* * * * *